United States Patent [19]

Kobayashi et al.

[11] Patent Number: 5,501,988
[45] Date of Patent: Mar. 26, 1996

[54] ANTI HCG-β CORE MONOCLONAL ANTIBODY, ITS PRODUCTION AND USE

[75] Inventors: Kiyoshi Kobayashi; Makoto Katsuno; Takahisa Kobayashi, all of Nagano, Japan

[73] Assignee: Wako Pure Chemical Industries, Ltd., Osaka, Japan

[21] Appl. No.: 48,963

[22] Filed: Apr. 12, 1993

Related U.S. Application Data

[63] Continuation of Ser. No. 581,111, Sep. 12, 1990, abandoned.

[30] Foreign Application Priority Data

Oct. 4, 1989 [JP] Japan .................................. 1-259293

[51] Int. Cl.$^6$ ............................ G01N 33/53; C12N 5/20; C07K 16/26
[52] U.S. Cl. .................. 436/548; 435/7.92; 435/7.93; 435/7.94; 435/70.21; 435/172.2; 435/240.27; 436/528; 436/534; 436/813; 436/817; 530/388.24; 530/391.1; 530/391.3
[58] Field of Search .................... 435/7.1, 7.92, 435/7.93, 7.94, 70.21, 172.2, 240.26, 240.27; 436/518, 528, 534, 548, 811, 813, 817; 530/388.1, 388.24, 391.1, 391.3

[56] References Cited

PUBLICATIONS

Norman et al. *J. Clin. Endocrin. Metab.* vol. 61., No. 6, pp. 1031–1038. (1985).

Cole et al., Molecular Endocrinology, vol. 2, No. 9, 825–830 (1988).

Bidart et al., J. Biol. Chem., vol. 262, No. 18, 8551–8556 (1987).

Chemical Abstracts 113:34783z (1990).

Ryuuichi Nishimura et al., 9th Meeting of Study Group of Tumor Markers, Program and Abstracts of Presentation, Nagoya, Japan, Oct. 22, 1989 (with translation).

Steven Birken et al., Endocrinology, 123, 572–583, 1988.

Alexander Krichevsky et al., Endocrinology, 123, 584–593, 1988.

H. R. Masure et al., Journal of Clinical Endocrinology and Metabolism, 53, 1014–1020, 1981.

Laurence A. Cole et al., Cancer Research, 48, 1356–1360, 1988.

*Primary Examiner*—Toni R. Scheiner
*Assistant Examiner*—Susan C. Wolski
*Attorney, Agent, or Firm*—Wenderoth, Lind & Ponack

[57] ABSTRACT

A hybridoma capable of producing monoclonal antibody for recognizing hCG-β core region and hCG-β subunit, which is obtained by cell fusion of an antibody producing cell of a mammal immunized with hCG-β subunit and a lymphoid cell line, and the monoclonal antibody are disclosed. The monoclonal antibody can be used in an immunochemical determination method useful for diagnosis of cancers.

15 Claims, 3 Drawing Sheets

ANTI HCG-β CORE MONOCLONAL ANTIBODY, ITS PRODUCTION AND USE

This application is a continuation of now abandoned application, Ser. No. 07/581,111, filed Sep. 12, 1990.

FIELD OF THE INVENTION

The present invention relates to a novel hybridoma which produces a monoclonal antibody for recognizing human chorionic gonadotropin β subunit core fragment (hereinafter abbreviated as hCG-β core) and the β subunit itself, and relates to the monoclonal antibody. Further, the present invention relates to an immunochemical determination method using the monoclonal antibody, and a reagent for the determination.

BACKGROUND OF THE INVENTION

Human chorionic gonadotropin (hereinafter abbreviated as hCG) is a kind of protein hormone which is produced from trophoblastic cells formed upon pregnancy, and it promotes secretion of progesterone. The detection of hCG is generally utilized for a primary diagnosis of pregnancy. Further, in chorionic diseases such as hydatid mole, destructive mole, choriocarcinoma and the like, it has been found that the determination of hCG in body fluids such as urine, blood and the like is of extreme importance from the viewpoints of early discovery, judgment of therapeutic effects and prognostic control of these diseases. However, in order to diagnose these diseases, it is necessary to determine a very small amount of hCG such as about 100 IU/liter or less. In this respect, a problem is immunological cross reactions with protein hormones having structures similar to that of hCG, namely, luteinizing hormone (hereinafter sometimes abbreviated as hLH), follicle-stimulating hormone (hereinafter sometimes abbreviated as hFSH) and thyroid-stimulating hormone (hereinafter sometimes abbreviated as hTSH). Particularly, hLH has very high similarity to hCG and a hLH concentration in urine sometimes reaches 150 IU/liter depending upon physiological conditions. Therefore, in order to determine hCG in a small amount of a body fluid, it is necessary to immunologically distinguish hCG from hLH.

On the other hand, according to the chemical analysis of these protein hormones, it has been found that the cross reactivity is due to their respective α-subunit parts which have many common structures. Thus, attempts have been made to specifically detect hCG by isolating and purifying β-subunit of hCG (hereinafter sometimes abbreviated as hCG-β), which has relatively less similarity, and producing an anti-hCG-β antibody.

However, the cross reactivity to hLH can not be completely eliminated by using the anti-hCG-β antibody because there still exists a common amino acid sequence in both β-subunits of hCG and hLH. On the other hand, a peptide composed of about 30 amino acids located at the C-terminal of hCG-β has an amino acid sequence which does not exist in hLH and it has become possible to completely distinguish hCG from hLH by utilizing this part. An antibody to the C-terminal region of hCG-β reacts with only hCG-β, and it does not undergo cross reaction with hLH. Further, as an advance in studies on hCG-β, it has been presumed that a hCG-β core region (hereinafter sometimes abbreviated as β core) must be present. Namely, it has been shown that β core is a glycoprotein composed of two peptides bound to each other through disulfide bond(s), one peptide of which is composed of the 6th to 40th amino acid residues of human chorionic gonadotropin β subunit (hCG-β) and the other is composed of the 55th to 92nd amino acid residues of hCG-β, and having a molecular weight of 12 to 17 kilodaltons (Endocrinology, 123, 572, 1988), and is present in urine of patients with not only obstetrical and gynecological malignant tumors such as ovarian cancer, cervical cancer or corpus utericancer but also various malignant tumors such as stomach cancer, kidney cancer and the like [J. Clin. Endocrinol. Metab., 53, 1014, 1981; Cancer, 45, 2583, 1980; Acta Endocrinol. (Copenh), 112, 415, 1986]. However, there is no established theory of its production, secretion and physiological significance, and there is no biological determination method of β core. Although a radioimmunoassay (RIA) using a polyclonal anti-hCG-β antibody referred to as SB6 has been established (Am. J. Obstet. Gynecol., 113,751, 1972) as an immunological determination method, β core can not be distinguished from human chorionic gonadotropin and hCG-β because there is no difference between the affinity of the antibody to β core and that to human chorionic gonadotropin and hCG-β.

Recently, monoclonal antibodies B202 and B204 for recognizing β core have been prepared by using β core as an immunogen (Endocrinology, 123, 584, 1988) and radioimmunoassay of β core has been reported (Cancer Res., 48, 1361, 1988; Cancer Res., 48, 1356, 1988).

However, SB6 is a polyclonal antibody and, when it is used in a radioimmunoassay, the antibody has similar affinity for β core, hCG and hCG-β, and has about 10% of cross reactivity to hLH.

B202, B204 and the like are monoclonal antibodies obtained by immunizing with β core. A. Krichevsky et al. have prepared several monoclonal antibodies to β core and have reported their properties in Endocrinology, 123, 584–593, 1988. However, in this paper, they have clearly described that no antibody to β core has been obtained in the case of using hCG-β as an immunogen.

On the other hand, in the field of clinical test, a novel monoclonal antibody to β core having a high affinity, which enables a high sensitivity assay, has been requested.

In addition, in the conventional RIA of β core, the assay system is assembled to determine only a urine specimen, and it is insufficient to determine a humoral tissue fluid, a tissue extract fluid and a tissue culture supernatant which are essential to study biosynthesis, secretion, distribution, metabolism and physiobiological effects of β core as well as relation to diseases and the like.

OBJECTS OF THE INVENTION

The present inventors have found that, different from monoclonal antibodies prepared by the conventional method for producing an anti-β core monoclonal antibody, a monoclonal antibody obtained by immunizing an animal with hCG-β as an immunogen and conducting cell fusion does not react with hCG and other protein hormones having similar structures, but recognizes β core and hCG-β, and further found that the use of the monoclonal antibody is of extreme importance as a diagnostic agent.

One object of the present invention is to provide a novel hybridoma which produces a novel monoclonal antibody for recognizing hCG-β core and hCG-β.

Another object of the present invention is to provide the novel monoclonal antibody.

Still another object of the present invention is to provide an immunochemical determination method using the novel monoclonal antibody.

Still another object of the present invention is to provide a reagent for the determination using the novel monoclonal antibody.

These objects as well as other objects and advantages of the present invention will become apparent to those skilled in the art from the following description with reference to the accompanying drawings.

SUMMARY OF THE INVENTION

Figure 1:
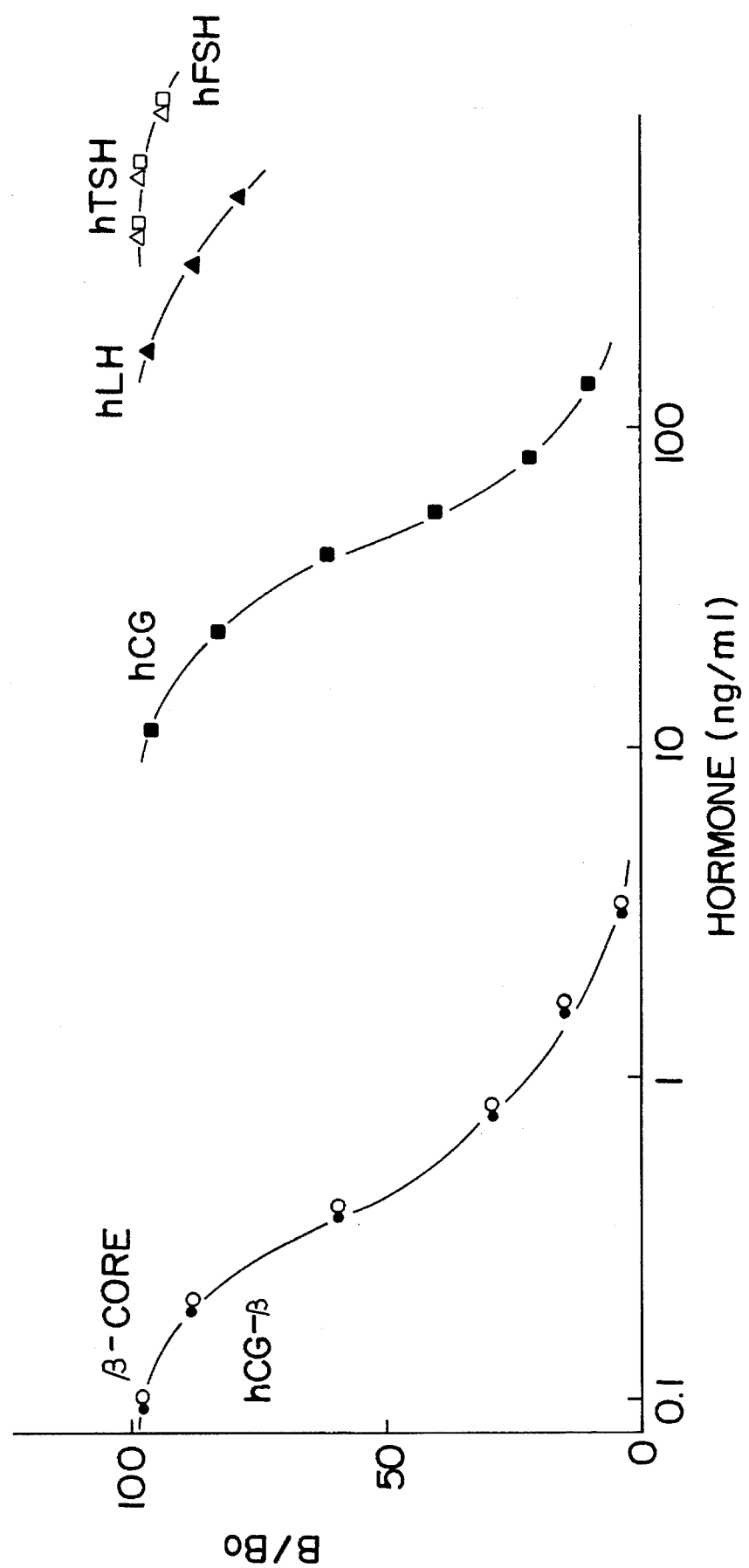
FIG. 1 is a graph illustrating the reactivity of the monoclonal antibody of the present invention to β core (o), hCG-B (●), hCG (■) and various glycoprotein hormones.

According to the present invention, there are provided:

(1) A hybridoma being capable of producing a monoclonal antibody for recognizing hCG-β core region and hCG-β subunit which is obtained by cell fusion of an antibody producing cell of a mammal immunized by hCG-β subunit and a lymphoid cell line;

(2) A monoclonal antibody produced by the hybridoma of the above (1); and (3) An immunological determination method which comprises detecting and measuring a substance which can immunologically react with the monoclonal antibody of the above (2) by using the monoclonal antibody. Examples of such a substance include those containing β core region and/or hCG-β subunit which can be recognized by the monoclonal antibody, such as β core itself, hCG-β and the like.

DETAILED DESCRIPTION OF THE INVENTION hCG-β to be used for the production of the hybridoma of the present invention can be prepared by a known method. For example, hCG-β can be obtained by purification from concentrated and purified hCG from urine of pregnant women according to the method described by F. J. Morgan et al., Endocrinology, 88, 1045–1053, 1971, wherein naturally occurring hCG is dissociated into hCG-α and hCG-β, for example, by dissolving it in 10M urea and the mixture is applied to a column packed with DEAE-Sephadex A-25 to obtain a hCG-β fraction. More specifically, 400 mg of native hCG (Bell et al., Endocrinology, 84, 298, 1969) is dissolved in 15 ml of 10M urea adjusted to pH 4.5 with HCl, and incubated for 1 hour at 40° C. 3.0 ml of 0.03 M glycine was then added, and the pH adjusted to pH 7.5 with NaOH. Chromatography was performed on DEAE-Sephadex A-25 (2.5×20 cm) equilibrated with 0.03M glycine-8M urea, pH 7.5. Initial elution was performed with the equilibrating buffer. After the first peak had emerged, the second was eluted by a stepwise change to 0.2M glycine-t M NaCl-8M urea, pH 7.5. Protein containing tubes were acidified, pooled, dialyzed for 12 hours against 1% acetic acid, and then against water for 12 hours before lyophilization. In this manner, the subunits of the hCG were separated.

In immunization, hCG-β, a product obtained by binding hCG-β to a polymer carrier or both can be used as an immunogen.

The binding between the peptide and a polymer carrier used herein can be formed by the conventional method (e.g., Hormone and Metabolic Research, 8, 241, 1976). Examples of a reagent to be used for binding include glutaraldehyde, water-soluble carbodiimide and the like. Examples of the polymer carrier include bovine thyroglobulin, bovine serum albumin, bovine gamma globulin, hemocyanin and the like. The proportion of the peptide to the polymer carrier is preferably 1:1 to 1:4 and, in many cases, good results can be obtained by carrying out the reaction at a neutral pH range, particularly, at about pH 7.3. Further, in many cases, good results can be obtained by carrying out the reaction for 2 to 6 hours, particularly, 3 hours. The product thus obtained can be stored by dialyzing it against water at about 4° C. according to the conventional method and then frozen, or by lyophilization.

As the animal to be immunized, experimental animals, for example, mouse, rat, hamster and the like can be advantageously used and, particularly, mouse is preferred. As the antibody producing cell, spleen cells of immunized animals are advantageously used. It may be a human spleen cell line.

Various combinations of animal cells to be immunized and lymphoid cell lines which are fused with the animal cells are possible. Among them, preferred examples thereof include cell fusion of mouse cells, which has brought about best results in various cell fusion experiments and provided advantageous cell fusion efficiency and the like, namely, cell fusion between an antibody producing cell of mouse hyperimmunized with an antigen, and mouse myeloma cell having excellent cell fusion efficiency proliferation properties and the like, particularly, homogeneous or heterogeneous myeloma, preferably, homogeneous myelomas having markers such as hypoxanthine guanine phosphoribosyltransferase deficiency (HGPRT⁻) or thymidine kinase deficiency (TK⁻) [e.g., P3-X 63-Ag.8, U1 (Ichimori et al., Journal of Immunological Method, 80, 55, 1985), P3-X63-Ag8-6.5.3 (Shulman, M. et al., Nature, 276, 269, 1978), mouse myeloma cell SP2/0-Ag14 (SP2), Nature, 276, 269, 1978] and the like.

In addition, human lymphoid cells may be also used. In this case, a cell line obtained and established from human being can be advantageously used.

In order to obtain the monoclonal antibody, rat and mouse are preferred. For example, when immunizing mouse, any route such as subcutaneous, intraperitoneal, intravenous, intramuscular, intracutaneous or the like can be employed. Particularly, subcutaneous, intraperitoneal or intravenous injection, especially, subcutaneous injection is preferred. Further, intervals for inoculation, inoculation amounts and the like can be varied and various methods can be employed. For example, an immunogen can be inoculated every two weeks for 2 to 8 times, and spleen cells removed 1 to 5 days, preferably, 2 to 4 days after the final immunization can be suitably used. The desired amount of inoculation is 0.1 μg or more, preferably, 10 to 100 μg as the amount of hCG-β per one inoculation per mouse.

When spleen cells are used as a lymphocyte source, it is preferable to conduct partial bleeding before the removal of spleen to confirm increase in the antibody titer in the blood, followed by cell fusion.

Cell fusion between lymphocytes and a lymphoid cell line can be conducted by, for example, fusing lymphocytes of an immunized mouse, particularly, those derived from the spleen, with a lymphoid cell line such as a myeloma of a homogeneous or heterogeneous animal, preferably, that of a homogeneous animal, having a marker, for example, hypoxanthine guanine phosphoribosyltransferase deficiency (HGPRT⁻) or thymidine kinase deficiency (TK⁻) (e.g. as in the above-cited Ichimori et al. and Shulman et al. publications). For cell fusion, an agent for fusion such as HVJ (Sendai) virus, polyethylene glycol (PEG) or the like can be used. Of course, it is possible to add a fusion promoting agent such as dimethylsulfoxide (DMSO) and the like. Usually, PEG having a polymerization degree of 1000 to 6000, the reaction time of 0.5 to 30 minutes and the concentration of 10 to 80% and the like are employed. As one example of preferred conditions, cell fusion is efficiently carried out by treatment with PEG 6000 in a concentration of 35 to 55% for 4 to 10 minutes. Fused cells (hybridomas) can be selectively proliferated by using hypoxanthine-aminopterinthymidine medium (HAT medium, Nature, 256, 495–497, 1975) or the like.

Serum of mouse and a culture supernatant of the resulting cells can be screened for capability of producing the desired antibody. A screening for antibody titer can be conducted as follows. Although the screening can be conducted by radioimmunoassay (RIA), enzyme immunoassay (EIA) and the like, various modifications of these assays are possible. As a preferred example of these assays, a method according to EIA is illustrated below. An anti-mouse immunoglobulin is immobilized to a solid phase according to the conventional method (for example, it is advantageous to use a microtiter plate having 96 wells as a solid phase because the measurement can be conducted quickly with a multiscanning apparatus or the like), and culture supernatant(s) or sera of mouse to be measured are added to the solid phase to react them at a constant temperature (hereinafter this means 4° to 40° C.) for a predetermined period of time. Then, the reaction product is thoroughly washed and hCG-β or β core labeled with an enzyme is added thereto. The mixture is reacted at a constant temperature for a predetermined period of time. After thoroughly washing the reaction product, a substrate for the enzyme is added and they are reacted at a constant temperature for a predetermined period of time. Then, a material produced is measured by means of its absorbancy, fluorescence intensity or the like. Preferably, cells in wells which proliferate in a selective medium and show antibody activities against β core are cloned by limiting dilution and the like. A supernatant of the cloned cells are subjected to the similar screening to increase the number of cells in wells having a high antibody titer. Thereby, a hybridoma clone producing the desired monoclonal antibody of the present invention can be obtained.

The anti-hCG-β core monoclonal antibody of the present invention can be obtained by proliferating the hybridoma thus cloned in a liquid medium or in the abdominal cavity of a mammal. For example, the monoclonal antibody can be obtained from a culture medium resulted from cultivation of the cells in a liquid medium such as that obtained by adding 0.1 to 40% bovine serium to RPMI-1640 for 2 to 10 days, preferably, 3 to 5 days. In addition, a large amount of the antibody having a much higher titer in comparison with that obtained from a supernatant of cell culture can be obtained by inoculating the cells in the intraperitoneum of a mammal such as mouse or the like to proliferate the cells and collecting the acites fluid. For example, in the case of mouse, $1\times10^4$ to $1\times10^7$ cells, preferably, $5\times10^5$ to $2\times10^6$ cells of the hybridoma are inoculated into the intraperitoneum or the like of BALB/c mouse or the like wherein a mineral oil or the like has been inoculated and, after 7 to 20 days, preferably, 10 to 14 days, the acites fluid or the like is collected. The antibody produced and retained in the acites fluid can be readily isolated and purified by, for example, ammonium sulfate fractionation, DEAE-cellulose column chromatography, protein A Sepharose column chromatography and the like to obtain the monoclonal antibody as a pure immunoglobulin.

The anti-hCG-β core monoclonal antibody of the present invention has the following properties:

(1) It has a reactivity to β core;

(2) It has a reactivity to hCG-β;

(3) It has a reactivity to urine of a human patient with a high probability of cancer;

(4) It has a reactivity to serum of a human patient with a high probability of cancer; and (5) Its class of antibody is IgGl.

The antibody to be used for detection and determination as described hereinafter may be a fraction and examples of the fraction include Fab, Fab', F(ab')$_2$ and the like.

The monoclonal antibody of the present invention is very useful for diagnosing cancers by means of recognition of β core region in a system utilizing immunochemical techniques such as EIA, ELISA, RIA and the like.

In general, these immunochemical techniques can be divided into the following classes:

(1) Competitive method: A specimen solution containing an unknown amount of antigen and a predetermined amount of antigen labeled with a labeling agent are competitively reacted with a predetermined amount of the corresponding antibody. Then, the activity of the labeling agent which is bound or not bound to the antibody is determined.

(2) Sandwich method: To a specimen solution containing an unknown amount of antigen is added an excess amount of antibody held on a carrier to react them (first reaction) and a predetermined excess amount of antibody labeled with a labeling agent is added to the reaction mixture to react them (second reaction). The activity of the labeling agent which is held or not held on the carrier is determined. The first and second reactions can be carried out simultaneously or separately.

In the immunological determination method of the present invention, either (1) or (2) can be employed. However, the method according to the sandwich method of (2) is more effective. In the sandwich method, the antigen determination site of the antibody originally held on the carrier should not overlap that of the antibody bound to the labeling agent. One antibody should be the monoclonal antibody of the present invention which can react with β core. The other antibody may be a monoclonal or polyclonal antibody in so far as it can react with hCG-β. The antibody which can react with hCG-β can be prepared by a known method. For example, in the case of a polyclonal antibody, it can be prepared by immunizing a mammal such as rabbit or the like several times with a complex of hCG-β and a carrier protein as an immunogen and purifying the resulting antiserum by hCG-β immobilized affinity column chromatography to obtain an anti-hCG-β antibody.

For purification of β core which is used for labeling or standardization, the conventional manner can be employed. Namely, as described in Endocrinology, 123,572– 583, 1988, β core can be obtained from a commercially available partially purified hCG by subjecting it to gel chromatography and immunoaffinity chromatography.

Examples of a specimen from a patient to be subjected to the detection and determination of the present invention include body fluids such as serum, urine, cerebrospinal fluid and the like, as well as, in some cases, tissues and their extracts and the like.

Hereinafter, as an example of the determination method of the present invention according to EIA, a method using peroxidase as the labeling agent is illustrated in detail. However, the determination method of the present invention is not limited to that using peroxidase.

(1) Firstly, a specimen is added to an antibody held on a carrier to cause a binding reaction. Then, an antibody bound to peroxidase is added thereto to further react them.

(2) To the reaction product obtained in (1) is added substrate(s) for peroxidase and the absorbancy or fluorescence intensity of the resulting material is measured to determine the enzymatic activity of the above reaction product.

(3) In advance, the above operations of (1) and (2) are conducted with respect to standard solution(s) containing predetermined amount of a substance reactive with the antibody to prepare a standard curve of the relation between the amount of the substance to the absorbancy or fluorescence intensity.

(4) Regarding the specimen which contains an unknown amount of the substance, the absorbancy or fluorescence intensity obtained is compared with the standard curve to determine the amount of the substance which has reacted with the monoclonal antibody in the specimen.

Hereinafter, as an example of the determination method of the present invention according to RIA, a method using $^{125}I$ as the labeling agent is illustrated in detail. However, the determination method of the present invention is not limited to that using $^{125}I$.

(1) Firstly, a specimen is added to an antibody held on a carrier to cause a binding reaction. Then, $^{125}I$ labeled antibody is added thereto to further react them.

(2) γ-Radioactivity of the reaction product obtained in the above (1) is measured.

(3) In advance, the above operations of (1) and (2) are conducted with respect to standard solution containing predetermined amount(s) of a substance reactive with the antibody to prepare a standard curve of the relation between the amount of the substance and the γ-radioactivity.

(4) Regarding the specimen which contains an unknown amount of the substance, the γ-radioactivity obtained is compared with the standard curve to determine the amount of the substance in the specimen.

Examples of the labeling agent include fluorescent materials, luminous materials and the like in addition to enzymes and radioisotopes.

As the radioisotopes, $^{125}I$, $^{131}I$, $^{3}H$, $^{14}C$ and the like can be used. As the enzymes, those being stable and having larger specific activities are preferred. Examples of the enzymes include (1) carbohydrases [e.g., glycosidases (e.g., β-galactosidase, β-glucosidase, β-glucuronidase, β-fructosidase, α-galactosidase, α-glucosidase, α-mannosidase), amylases (e.g., α-amylase, β-amylase, isoamylase, glucoamylase, Taka-amylase A), cellulase, lysozyme], (2) amidases (e.g., urease, asparaginase), (3) esterases [e.g., cholinesterases (e.g., acetylcholinesterase), phosphatases (e.g., alkaline phosphatase), sulfatase, lipase], (4) nucleases (e.g., deoxyribonuclease, ribonuclease), (5) iron-porphyrins enzymes (e.g., catalase, peroxidase, cytochrome oxidase), (6) copper enzymes (e.g., tyrosinase, ascorbate oxidase), (7) dehydrogenases (e.g., alcohol dehydrogenase, malate dehydrogenase, lactate dehydrogenase, isocitrate dehydrogenase) and the like. Examples of the fluorescent material include fluorescamine, fluorescein isothiocyanate and the like. Examples of the luminous material include luminol, luminol derivatives, luciferin, lucigenin and the like.

For binding the antibody to the labeling agent, the conventional methods such as chloramine T method (Nature, 194, 495, 1962), periodate method (Journal of Histochemistry and Cytochemistry, 22, 1084, 1974), maleimide method (Journal of Biochemistry, 79, 233, 1976) and the like can be employed.

For conducting the specific immunochemical determination method of the present invention according to the sandwich method, a solid phase wherein an antibody is physically or chemically bound to a carrier is added to a specimen containing an unknown amount of β core to react them (first reaction). After washing the solid phase, a predetermined amount of an antibody labeled with a labeling agent is added to the solid phase to react them (second reaction). Then, usually, after thoroughly washing the solid phase, the activity of the labeling agent bound to the solid phase is measured. When the labeling agent is a radioisotope, the measurement is carried out with a well counter or a liquid scintillation counter. When the labeling agent is an enzyme, substrate(s) is added to the reaction mixture and allowed to stand. The enzymatic activity is determined by a colorimetric or fluorescence method. When the labeling agent is a fluorescent or luminous material, it can be determined according a known method. In these determination methods, washing between the first and second reactions can be omitted. For further simplification, a specimen, an antibody bound to a solid phase and an antibody labeled with a labeling agent can be mixed to react them, simultaneously. Namely, the antibodies used in the present invention have different antigen determination sites and, thereby, the present invention has the very useful characteristic point such as the result of the determination is not influenced by the order of addition of reagents, time required for addition, presence or absence of a washing step and the like.

Thus, the determination method of the present invention has the following advantages:

(1) A very small amount of β core and hCG-β can be determined without any influence of peptide hormones such as hCG, hLH and the like;

(2) As a specimen from a patient to be determined, materials other than urine such as serum and the like can be used, although urine is particularly suitable; and (3) Various malignant tumors, particularly, cancers in the obstetrical and gynecological field and those relating to genital organs are selected as the objective diseases to be determined, and the method is highly applicable to diagnosis and prognosis control of these diseases.

In order to carry out the immunochemical method for determination of β core region of the present invention, for example, by the sandwich method, a kit of reagents can be used. As such a kit, that comprising the following reagents (1) to (6) can be exemplified:

(1) An antibody held on a carrier;
(2) A labeled antibody;
(3) Standard S core or hCG-β;
(4) Buffer solution(s) for diluting these reagents (1) to (3) and a specimen (the buffer may be any buffer which can be used for diluting these reagents and a specimen and one example thereof is a phosphate or glycine buffer solution of pH 6 to 9);
(5) Buffer solution(s) for washing the carrier after incubation (the buffer may be any buffer which can be used for washing the carrier and one example thereof is a phosphate or glycine buffer solution); and
(6) In the case of using an enzyme as a labeling agent, reagents for measuring the enzyme [for example, in the case of peroxidase, when a fluorescence method is employed, p-hydroxyphenylacetic acid as the substrate of the enzyme and hydrogen peroxide, and, when colorimetric method is employed, o-phenylenediamine as the substrate of the enzyme and hydrogen peroxide; a buffer solution for dissolving the substrate (preferably, a phosphate buffer solution); and an agent for stopping the enzymatic reaction].

For example, this kit can be used as follows:

The standard β core, hCG-β or specimen (about 10 to 200 µl) is diluted with the reagent (4). A predetermined amount of the reagent (1) is added to the diluted solution and the reaction is carried out at about 0° to 40° C. for about 1 to 48 hours. After washing the carrier with water, the reagent (2) (about 10 to 300 µl) is added and the reaction is conducted at about 0° to 40° C. After the reaction for about 1 to 48 hours, the carrier is washed with water and the peroxidase activity bound to the carrier is measured. Namely, a solution for a substrate of peroxidase (about 10 to 1000 µl) is added and the reaction is conducted at about 20° to 40° C. for about 0.1 to 2 hours. Then, the reaction is stopped and an absorbancy or fluorescence intensity of the reaction mixture is measured.

According to the immunochemical determination method of the present invention, as the monoclonal antibody of the present invention reacts both with β core and hCG-β and has no cross-reactivity with hLH, hFSH and hTSH, it is possible to determine β core, hCG-β or both β core and hCGB-β concurrently in a high sensitivity with one measurement by a simple technique in a normal clinical test.

As described hereinabove, the monoclonal antibody of the present invention has a high reactivity with urine, serum and the like of patients with various cancers and, therefore, it is advantageously used as a diagnostic agent of cancers and the like.

Further, a very high sensitive determination can be conducted within a short period of time with the reagent for immunochemical determination of the present invention using the monoclonal antibody, and a level of normal healthy people can be determined.

Thus, by establishing the determination reagent according to the present invention, not only promotion of fundamental researches of β core such as its biosynthesis, secretion, metabolism and the like is expected, but also, as the present determination method gives high positive and precise results, it becomes possible to simply and exactly make diagnosis of various cancers in addition to malignant tumors in the obstetrical and gynecological field, and observe the progress of treatment of such diseases.

The following Examples further illustrate the present invention in detail but are not to be construed to limit the scope thereof.

EXAMPLE 1

Preparation of Hybridoma

Five BALB/c mice were intraperitoneally injected with a suspension of hCG-β (100 µg per mouse) dissolved in physiological saline (0.5 ml) and Freund's complete adjuvant (0.5 ml). After 2 to 12 weeks, each mouse was intravenously injected at the caudal vein with a booster of hCG-β (50 µg) dissolved in physiological saline (0.25 ml). The spleen cells of the mice were removed 3 days after the final immunization to conduct cell fusion.

The spleen cells collected ($1.0 \times 10^8$ cells) and myeloma cell P3X63Ag8U1 ($1.0 \times 10^7$ cells) were mixed in RPMI-1640 medium and the mixture was centrifuged at 1000 rpm for 5 minutes. To the resulting pellet was slowly added 50% polyethylene glycol 1500 (1 ml) at 37° C. over 1 minute to fuse the cells. RPMI-1640 (7 ml) at 37° C. was added over 5 minutes and the mixture was centrifuged. The fused cells thus obtained were diluted with HAT medium (30 ml) and 0.1 ml portions thereof were distributed into wells of a 96 well microtiter plate. Then, the cultivation was continued, while a half of HAT medium was replaced with a fresh HAT medium every 2 to 3 days, After 7 to 14 days, hybridomas were proliferated in about 60% of all 288 wells (170/288) and 40% of these wells (68/170) produced anti-hCG-β antibody. Further, about 30% of the latter wells (17/68) showed β core binding activity.

The cells in the well showing the highest antibody titer were cloned by limiting dilution. Namely, BALB/c mouse thymocytes ($10^5$ cells/well) as feeder cells and the hybridoma (1 cell/well) were added to wells and they were cultivated in HT medium. This operation was repeated twice. A clone which most stably produced a large amount of the antibody was selected by cloning and named as 229. According to the same operation, hybridoma 233 was established.

The hybridoma 229 has been deposited at Fermentation Research Institute, Agency of Industrial Science and Technology (FRI), 1-3, Higashi 1-chome, Tsukuba-shi, Ibaraki-ken 305, Japan, under the Budapest treaty since Sep. 26, 1989 under the accession number of FERM BP- 2614.

The measurement of antibody titer was conducted as follows:

A culture supernatant of a hybridoma (50 µl) was added to anti-mouse immunoglobulin (IgG+IgM+IgA) antibody immobilized on a microtiter plate and reacted at 4° C. for 1 day. After washing, hCG-β or β core labeled with peroxidase was added and further reacted at 4° C. for 1 day. After washing, a solution of enzyme substrate, o-phenylenediamine (hereinafter abbreviated as OPD) and the absorbancy was measured to determine the antibody titer of the culture supernatant of the hybridoma.

The antigen labeled with peroxidase was prepared as follows:

A solution of N-succinimide 4-(N-maleimidomethyl)cyclohexanoate solution (100 µl) was added to hCG-β or β core (500 µg/ml) and the mixture was reacted at room temperature for 90 minutes. The reaction mixture was subjected to gel filtration by passing through a Sephadex G- 25 column to obtain a maleimidated antigen. Horseradish peroxidase (7 mg) dissolved in 0.02M phosphate buffer solution containing 0.1M sodium chloride was reacted with 20-fold amount of N-succinimidyl-3-(2-pyridylthio)propionate at room temperature for 1 hour. Further, dithiothreitol (0.25 ml) dissolved in 0.1M acetate buffer (pH 4.5) was added and the mixture was reacted at room temperature for 30 minutes. The latter reaction mixture was subjected to gel filtration by passing through a Sephadex G-25 column and the filtrate was mixed with the above maleimidated antigen. After reaction at 4° C. for 20 hours, the reaction mixture was subjected to gel filtration with Ultragel AcA-44 to purify the antigen.

EXAMPLE 2

Preparation of Monoclonal Antibody

BALB/c mouse pre-treated by intraperitoneal administration of pristane (0.5 ml) was intraperitoneally injected with hybridoma 229 ($5 \times 10^6$ cells) suspended in RPMI-1640 (0.5 ml). After 10 to 14 days, the acites fluid retained was collected and purified by protein A-Sepharose to obtain monoclonal antibody 229. The yield of monoclonal antibody 229 was 3.5 mg per 1 ml of the fluid.

The isotype of this monoclonal antibody was determined as $IgG_1$ according to Ouchterlony's method. The reactivity thereof was determined by testing for cross reactivity with β core, hCG-β as well as chorionic and pituitary glycoprotein hormones according to EIA.

The results are shown in FIG. 1. The monoclonal antibody reacts with β core and hCG-β in almost the same intensities, and hardly reacts with human chorionic gonadotropin. On the other hand, monoclonal antibody 233 which is obtained by using hybridoma 233 according to the same manner does not cause a competitive reaction in the above EIA, even if it is added together with monoclonal antibody 229. Therefore, it is considered that monoclonal antibody 233 would recognize an epitope of β core different from that recognized by monoclonal antibody 229.

EXAMPLE 3

Preparation of Kit (1) Preparation of Immobilized Antibody

Polystyrene beads (¼ inch in diameter, manufactured by Precision Plastic Ball Company, Chicago, U.S.A.) (50 beads) were placed in 0.1M phosphate buffer (pH 7.0, 7.5 ml) and a monoclonal anti-β core antibody (monoclonal antibody 229) was added thereto. The mixture was allowed to stand at room temperature overnight. The polystyrene beads were washed with phosphate buffer. 0.1% of sodium azide was added and the beads were stored in a refrigerator.

(2) Preparation of antibody labeled by enzyme hCG-β (20 mg) and bovine serum thyroglobulin (20 mg) were dissolved in 0.05M phosphate buffer (pH 7.5) and glutaraldehyde was added to the solution so that the final concentration thereof became 0.2%. The mixture was reacted at 4° C. for 2 hours. The reaction mixture was dialyzed three times against distilled water (2 liter) at 4° C. and lyophilized to obtain hCG-β-bovine serum thyroglobulin complex (35 mg).

Rabbits were subcutaneously immunized at their back 6 times with the above complex (1 mg per 1 rabbit) together with Freund's complete adjuvant every 2 weeks. Exsanguination from carotid arteries was conducted to obtain anti-hCG-β rabbit serum.

Ammonium sulfate was added to anti-hCG-β rabbit serum (10 ml) so that the final concentration became 1.64M to conduct salting-out. The mixture was centrifuged at 10000 rpm for 10 minutes and the precipitate was dissolved in 0.02M borate buffer (pH 8.0, 5 ml). The solution was dialyzed against the same buffer. The supernatant was applied to a column (2.0×4.8 cm) packed with hCG-β binding Sepharose 4β equilibrated with the same buffer and eluted with 0.2M glycine-HCl buffer (pH 2.3) to obtain purified anti-hCG-β antibody (20 mg).

To anti-hCG-β antibody (20 mg) thus obtained was added pepsin from swine tunica mucosa ventriculi (0.4 mg) and the mixture was reacted in 0.1M acetate buffer (pH 4.5) at 37° C. for 16 hours. The reaction mixture was neutralized and applied on a column (1.9×90 cm) packed with Ultragel AcA-44 and eluted with 0.1M borate buffer (pH 8.0) to obtain F(ab')2 (10 mg). This F(ab')2 (10 mg) was dissolved in 0.1M phosphate buffer (pH 6.0) containing 2 mM EDTA. To the solution was added 2-mercaptoethylamine and the mixture was reacted at 37° C. for 90 minutes. Then, the reaction mixture was applied on a column (1×30 cm) packed with Sephadex G-25 and eluted with 0.1M phosphate buffer (pH 6.0) containing 2 mM EDTA to obtain Fab' (7 mg).

Horseradish peroxidase (10 mg) was dissolved in 0.1M phosphate butter (pH 6.8, 1.4 ml). To the solution was added a solution of N,N-dimethylformamide (80 μl) dissolved in N-succinimide 4-(maleimidomethyl)cyclohexanoate (9.7 mg) and the mixture was reacted at 30° C. for 1 hour. The reaction mixture was centrifuged and the resulting supernatant was applied on a column (1×30 cm) packed with Sephadex G-25 and eluted with 0.1M phosphate buffer (pH 6.8) to obtain a maleimidated peroxidase (7 mg).

The above-obtained Fab' (7 mg) and maleimidated peroxidase (7 mg) were reacted in 0.1M phosphate buffer (pH 6.5, 1 ml) at 4° C. for 20 hours. The reaction mixture was applied on a column (1.5×90 cm) packed with AcA-44 and eluted with 0.1M phosphate buffer (pH 6.5). Thus, the desired anti-hCG-β Fab' labeled with peroxidase (about 9 mg) was obtained.

EXAMPLE 4

Diagnosis of Cancers (1) Determination

A specimen or S core standard solution (100 μl) and 0.02M phosphate buffer (pH 7.5, 200 μl) containing 0.1% bovine serum albumin were placed in a test tube (12×75 mm) and one immobilized antibody (polystyrene bead) was added thereto. The test tube was allowed to stand at room temperature (20° to 30° C.) for 1 hour. After washing twice with purified water (4 ml), the reaction mixture was admixed with 0.02M phosphate buffer (pH 7.5, 300 μl) containing anti-hCG-β Fab'-peroxidase (about 50 ng) and 0.1% bovine serum albumin and allowed to stand at room temperature (20° to 30° C.) for 1 hour. The solution part was removed and the polystyrene bead was washed twice according to the same manner as that described above. The bead was transferred to another test tube. The peroxidase activity bound to the bead was determined by using OPD as the substrate in the presence of hydrogen peroxide and measuring absorbancy at 492 nm after standing in a dark place at room temperature for 30 minutes.

In the enzymatic immunological determination method of the present invention, the cross reactivity to hCG-β on the molar basis was about 100% and almost the same cross reactivity to β core was observed. On the other hand, the cross reactivities to glycoprotein hormones such as human chorionic gonadotropin, human luteinizing hormone, human follicle-stimulating hormone and human thyroid-stimulating hormone were very low such as 2.2%, 0.29%, less than 0.01% and less than 0.01%, respectively. The results are shown in FIG. 2.

Figure 2:
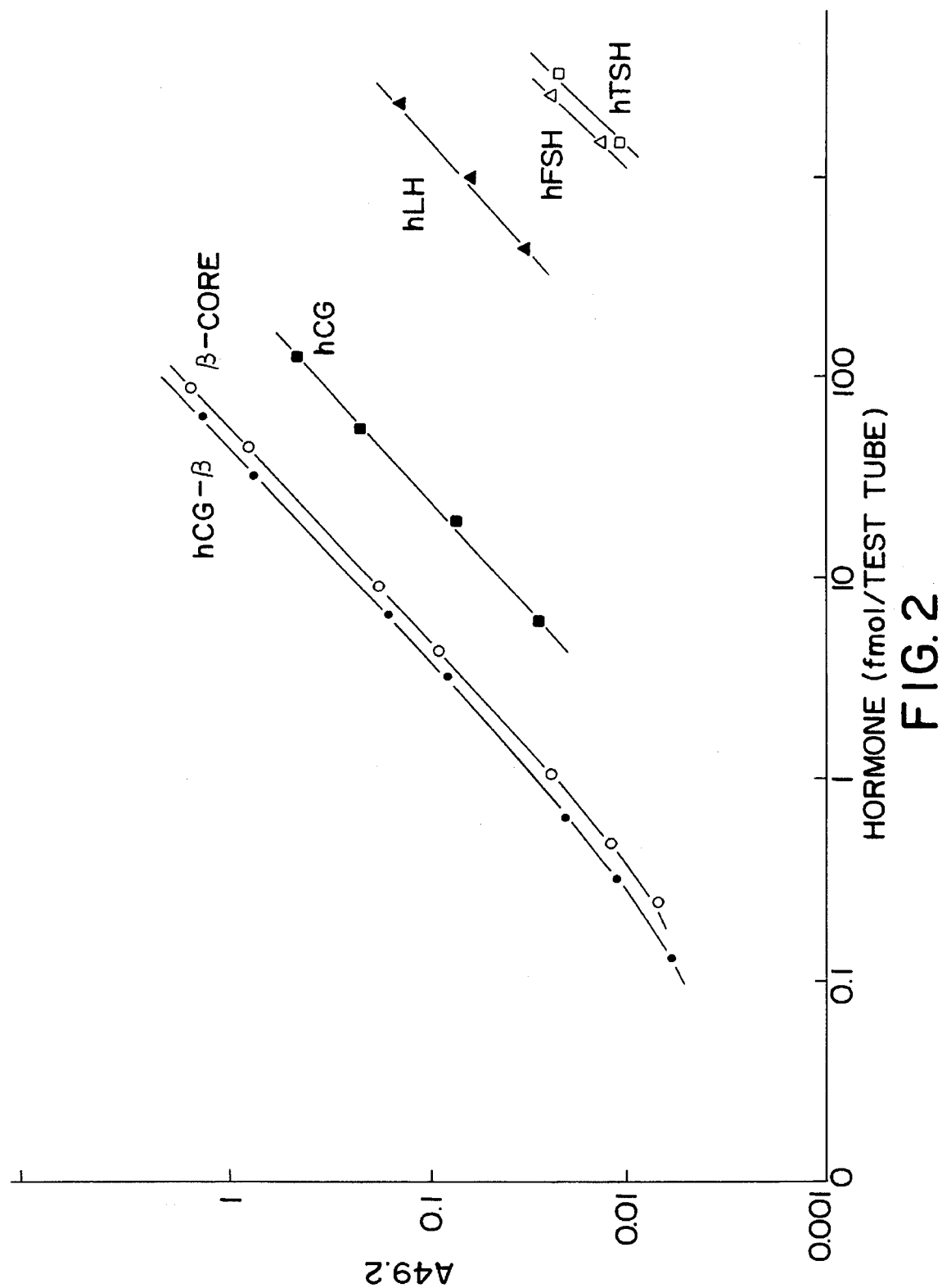
FIG. 2 is a graph illustrating the standard curve of β core (o) obtained by the reagent of the present invention as well as cross reactivity to hCG-β (●) and cross reactivity with various glycoprotein hormones of the reagent of the present invention.

The method had very high sensitivity such as the limit of the determination of S core 2 pg (0.13 fmol)/tube (20 pg/ml) (see FIG. 2).

The reactivity of the monoclonal antibody 281 produced by hybridoma 281 which recognizes hCG-β core region and is obtained by using purified β core as an immunogen was compared with the reactivity of the monoclonal antibody 229 of the present invention. When the reactivities to various protein hormones were compared according to a sandwich method using each monoclonal antibody as the immobilized antibody, the monoclonal antibody 229 showed almost the same reactivities to both β core and hCG-β core. On the other hand, in the case of the monoclonal antibody 281, when its reactivity to β core was taken as 100%, its reactivities to hCG-β and hCG were 14.0% and 1.2% respectively. Each reactivity to human luteinizing hormone, human follicle-stimulating hormone or human thyroid-stimulating hormone was 0.01% or less. According to these experimental results, it is considered that the monoclonal antibody 229 wherein the immunogen is hCG-β and the monoclonal antibody 281 wherein the immunogen is β core recognize different epitopes in the β core region.

(2) Urine β Core Level in Normal Healthy People

When β core level in urine of normal healthy people (n=231) was determined by using the reagent of the present invention, it was 0.18 ng/ml or less. When using the monoclonal antibody 281, it was 0.03 ng/ml or less.

(3) Determination of Urine and Sera of Patients with Various Diseases

β Core and/or hCG-β levels (ng/ml) in urine and sera of patients with various diseases were determined by using the reagent kit of the present invention. Further, as a control, β core levels were determined by using the monoclonal antibody 281 as the immobilized antibody. The results are shown in Table 1.

TABLE 1

| Specimen No. | Urine |  |  | Sera |  |  |
|---|---|---|---|---|---|---|
|  | Disease | Determn. | Control | Disease | Determn. | Control |
| 1 | lung cancer | 0.02 | 0.01 or less | liver cancer | 0.02 or less | 0.01 or less |
| 2 | ovarian cancer | 0.82 | 0.12 | ovarian cancer | 0.02 or less | 0.01 or less |
| 3 | large intestine cancer | 0.10 | 0.02 | stomach cancer | 2.00 | 0.02 |
| 4 | stomach cancer | 4.70 | 0.68 | lung cancer | 0.02 or less | 0.01 or less |
| 5 | uterus cancer | 0.35 | 0.02 | ovarian cancer | 1.10 | 0.02 |
| 6 | uterus cancer | 0.20 | 0.01 | ovarian cancer | 0.20 or less | 0.01 or less |
| 7 | uterus cancer | 3.91 | 0.68 | esophagus cancer | 1.00 | 0.02 |
| 8 | esophagus cancer | 2.00 | 0.08 | lung cancer | 0.20 | 0.01 |
| 9 | ovarian cancer | 0.44 | 0.02 | large intestine cancer | 0.34 | 0.01 or less |
| 10 | ovarium cancer | 0.15 | 0.01 or less | uterus cancer | 0.02 or less | 0.01 or less |
| 11 | ovarian cancer | 9.90 | 1.73 | uterus cancer | 0.02 or less | 0.01 or less |
| 12 | ovarian cancer | 1.15 | 0.27 | uterus cancer | 0.04 | 0.01 or less |
| 13 | hysteromyoma | 0.02 | 0.01 | hysteromyoma | 0.04 | 0.01 or less |
| 14 | pregnancy | 3321 | 20 | pancreas cancer | 0.72 | 0.02 |
| 15 | pregnancy | 805 | 15 | kidney cancer | 0.85 | 0.02 |
| 16 | stomach cancer | 0.02 | 0.01 or less | colitis | 0.07 | 0.01 or less |
| 17 | choriocarcinoma | 139 | 8.70 | stomach cancer | 0.11 | 0.01 or less |
| 18 | choriocarcinoma | 405 | 9.90 | large intestine cancer | 0.25 | 0.02 |
| 19 | uterus cancer | 0.44 | 0.14 | gastritis | 0.02 | 0.01 or less |
| 20 | uterus cancer | 0.21 | 0.02 | lung cancer | 0.44 | 0.02 |

As seen from Table 1, regarding urine specimens, high levels were observed in the case of pregnancy and, in patients with various cancers, 12 cases out of 17 cases (about 71%) showed levels higher than 0.2 ng/ml which was considered to be the cut-off level in view of the level of normal healthy people and, were determined to be positive. To the contrary, when β core levels were determined by using the monoclonal antibody 281 as the control, only 9 cases out of 17 cases (about 53%) showed levels higher than 0.03 ng/nl which was considered to be the cut-off level in view of the level of normal healthy people.

On the other hand, regarding sera specimens, in patients with various cancers, 8 cases out of 17 cases (about 47%) showed levels higher than 0.2 ng/ml, and were determined to be positive. This positive ratio of sera specimens is very high in comparison with that heretofore published in the prior art, about 10 to 20%.

Figure 3:
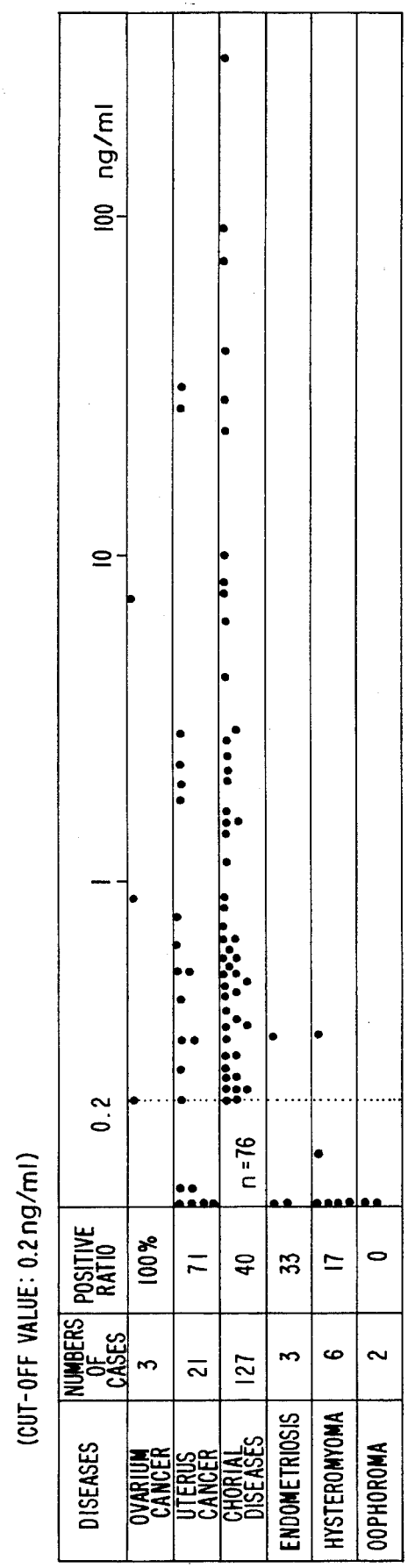
FIG. 3 is the results obtained by determining urines of patients with obstetrical and gynecological diseases.

Further, the results of the determination of urine from patients with obstetrical and gynecological diseases are shown in FIG. 3. Very high positive results were obtained in patients with ovarian cancer, uterus cancer and choriocarcinoma.

What is claimed is:

1. A hybridoma capable of producing a monoclonal antibody for recognizing hCG-β subunit, which is obtained by cell fusion of an antibody producing cell of a mammal selected from the group consisting of mouse, rat and hamster immunized with hCG-β subunit and a lymphoid cell line selected from the group consisting of a mouse myeloma cell line and a human cell line, wherein the monoclonal antibody has the following properties:

(1) specifically binds to hCG-β core region in urine or serum of a human patient with a cancer selected from the group consisting of ovarian cancer, cervical cancer, corpus utericancer, stomach cancer, kidney cancer and chorial diseases;

(2) specifically binds to hCG-β subunit in urine or serum of a human patient with a cancer selected from the group consisting of ovarian cancer, cervical cancer, corpus utericancer, stomach cancer, kidney cancer and chorial diseases;

(3) same degree of specific binding to hCG-β core region and hCG-β subunit;

(4) substantially less degree of specific binding to hCG than to the hCG-β core region or the hCG-β subunit; and (5) even less degree of specific binding to hLH than to hCG.

2. A hybridoma according to claim 1, wherein the antibody producing cell of a mammal is a mouse spleen cell.

3. A hybridoma according to claim 1, wherein the lymphoid cell line is a mouse myeloma cell line.

4. A hybridoma according to claim 1, which is FERM BP-2614.

5. A monoclonal antibody produced by a hybridoma which is obtained by cell fusion of an antibody producing cell of a mammal selected from the group consisting of mouse, rat and hamster immunized with hCG-β subunit and a lymphoid cell line selected from the group consisting of a mouse myeloma cell line and a human cell line, which monoclonal antibody has the following properties:

(1) specifically binds to hCG-β core region in urine or serum of a human patient with a cancer selected from the group consisting of ovarian cancer, cervical cancer, corpus utericancer, stomach cancer, kidney cancer and chorial diseases;

(2) specifically binds to hCG-β subunit in urine or serum of a human patient with a cancer selected from the group consisting of ovarian cancer, cervical cancer, corpus utericancer, stomach cancer, kidney cancer and chorial diseases;

(3) same degree of specific binding to hCG-β core region and hCG-β subunit;

(4) substantially less degree of specific binding to hCG than to the hCG-β core region or the hCG-β subunit; and (5) even less degree of specific binding to hLH than to hCG.

6. An immunological determination method, which comprises (a) reacting a specimen solution containing an unknown amount of hCG-β core region and hCG-β subunit, a predetermined amount of either or both of hCG-β core region and hCG-β subunit labeled with a labeling agent, and a predetermined amount of a monoclonal antibody, wherein the monoclonal antibody has the following properties:

(1) specifically binds to hCG-β core region in urine or serum of a human patient with a cancer selected from the group consisting of ovarian cancer, cervical cancer, corpus utericancer, stomach cancer, kidney cancer and chorial diseases;

(2) specifically binds to hCG-β subunit in urine or serum of a human patient with a cancer selected from the group consisting of ovarian cancer, cervical cancer, corpus utericancer, stomach cancer, kidney cancer and chorial diseases;

(3) same degree of specific binding to hCG-β core region and hCG-β subunit;

(4) substantially less degree of specific binding to hCG than to the hCG-β core region or the hCG-β subunit; and (5) even less degree of specific binding to hLH than to hCG, (b) determining the amount of the labeling agent which is either bound or not bound to the monoclonal antibody, and (c) determining the unknown amount of hCG-β core region and hCG-β subunit on the basis of the amount of the labeling agent obtained in (b).

7. The method according to claim 6 wherein the specimen solution is obtained from a human patient with a cancer selected from the group consisting of ovarian cancer, cervical cancer, corpus utericancer, stomach cancer, kidney cancer and chorial diseases.

8. An immunological determination method, which comprises (a) reacting a specimen solution containing an unknown amount of hCG-β core region and hCG-β subunit, and a predetermined amount of a monoclonal antibody which is immobilized on a carrier, wherein the monoclonal antibody has the following properties:

(1) specifically binds to hCG-β core region in urine or serum of a human patient with a cancer selected from the group consisting of ovarian cancer, cervical cancer, corpus utericancer, stomach cancer, kidney cancer and chorial diseases;

(2) specifically binds to hCG-β subunit in urine or serum of a human patient with a cancer selected from the group consisting of ovarian cancer, cervical cancer, corpus utericancer, stomach cancer, kidney cancer and chorial diseases;

(3) same degree of specific binding to hCG-β core region and hCG-β subunit;

(4) substantially less degree of specific binding to hCG than to the hCG-β core region or the hCG-β subunit; and (5) even less degree of specific binding to hLH than to hCG, (b) subsequently adding another antibody, which recognizes a different epitope of hCG-β core region and hCG-β subunit from an epitope which is recognized by the monoclonal antibody and is labeled with a labeling agent, to the resulting solution, (c) determining the amount of the labeling agent which is either bound or not bound to the carrier, and (d) determining the unknown amount of hCG-β core region and hCG-β subunit on the basis of the amount of the labeling agent obtained in (c).

9. The method according to claim 8, wherein the specimen solution is obtained from a human patient with a cancer selected from the group consisting of ovarian cancer, cervical cancer, corpus utericancer, stomach cancer, kidney cancer and chorial diseases.

10. An immunological determination method, which comprises (a) reacting a specimen solution containing an unknown amount of hCG-β core region and hCG-β subunit, a predetermined amount of a monoclonal antibody which is immobilized on a carrier, wherein the monoclonal antibody has the following properties:

(1) specifically binds to hCG-β core region in urine or serum of a human patient with a cancer selected from the group consisting of ovarian cancer, cervical cancer, corpus utericancer, stomach cancer, kidney cancer and chorial diseases;

(2) specifically binds to hCG-β subunit in urine or serum of a human patient with a cancer selected from the group consisting of ovarian cancer, cervical cancer, corpus utericancer, stomach cancer, kidney cancer and chorial diseases;

(3) same degree of specific binding to hCG-β core region and hCG-β subunit;

(4) substantially less degree of specific binding to hCG than to the hCG-β core region or the hCG-β subunit; and (5) even less degree of specific binding to hLH than to hCG, and another antibody which recognizes a different epitope of hCG-β core region and hCG-β subunit from an epitope which is recognized by the monoclonal antibody and is labeled with a labeling agent, (b) determining the amount of the labeling agent which is either bound or not bound to the carrier, and (c) determining the unknown amount of hCG-β core region and hCG-β subunit on the basis of the amount of the labeling agent obtained in (b).

11. The method according to claim 10, wherein the specimen solution is obtained from a human patient with a cancer selected from the group consisting of ovarian cancer, cervical cancer, corpus utericancer, stomach cancer, kidney cancer and chorial diseases.

12. An immunological determination method, which comprises (a) reacting a specimen solution containing an unknown amount of hCG-β core region and hCG-β subunit, and a predetermined amount of an antibody which is immobilized on a carrier, wherein the antibody recognizes hCG-β core region and hCG-β subunit, (b) subsequently adding another monoclonal antibody, which is labeled with a labeling agent, to the resulting solution, wherein the monoclonal antibody recognizes a different epitope of hCG-β core region and hCG-β subunit from an epitope which is recognized by the antibody and has the following properties:

(1) specifically binds to hCG-β core region in urine or serum of a human patient with a cancer selected from the group consisting of ovarian cancer, cervical cancer, corpus utericancer, stomach cancer, kidney cancer and chorial diseases;

(2) specifically binds to hCG-β subunit in urine or serum of a human patient with a cancer selected from the group consisting of ovarian cancer, cervical cancer, corpus utericancer, stomach cancer, kidney cancer and chorial diseases;

(3) same degree of specific binding to hCG-β core region and hCG-β subunit;

(4) substantially less degree of specific binding to hCG than to the hCG-β core region or the hCG-β subunit; and (5) even less degree of specific binding to hLH than to hCG, (c) determining the amount of the labeling agent which is either bound or not bound to the carrier, and (d) determining the unknown amount of hCG-β core region and hCG-β subunit on the basis of the amount of the labeling agent obtained in (c).

13. The method according to claim 12, wherein the specimen solution is obtained from a human patient with a cancer selected from the group consisting of ovarian cancer, cervical cancer, corpus utericancer, stomach cancer, kidney cancer and chorial diseases.

14. An immunological determination method, which comprises (a) reacting a specimen solution containing an unknown amount of hCG-β core region and hCG-β subunit, a predetermined amount of an antibody which is immobilized on a carrier, wherein the antibody recognizes hCG-β core region and hCG-β subunit, and another monoclonal antibody, which is labeled with a labeling agent, recognizes a different epitope of hCG-β core region and hCG-β subunit from an epitope which is recognized by the antibody, and has the following properties:

(1) specifically binds to hCG-β core region in urine or serum of a human patient with a cancer selected from the group consisting of ovarian cancer, cervical cancer, corpus utericancer, stomach cancer, kidney cancer and chorial diseases;

(2) specifically binds to hCG-β subunit in urine or serum of a human patient with a cancer selected from the group consisting of ovarian cancer, cervical cancer, corpus utericancer, stomach cancer, kidney cancer and chorial diseases;

(3) same degree of specific binding to hCG-β core region and hCG-β subunit;

(4) substantially less degree of specific binding to hCG than to the hCG-β core region or the hCG-β subunit; and (5) even less degree of specific binding to hLH than to hCG, (b) determining the amount of the labeling agent which is either bound or not bound to the carrier, and (c) determining the unknown amount of hCG-β core region and hCG-β subunit on the basis of the amount of the labeling agent obtained in (b).

15. The method according to claim 14, wherein the specimen solution is obtained from a human patient with a cancer selected from the group consisting of ovarian cancer, cervical cancer, corpus utericancer, stomach cancer, kidney cancer and chorial diseases.

* * * * *